(12) United States Patent
Staehle et al.

(10) Patent No.: US 9,283,225 B2
(45) Date of Patent: Mar. 15, 2016

(54) PYRIDO-PYRIMIDINE DERIVATIVES

(75) Inventors: Wolfgang Staehle, Ingelheim (DE);
Oliver Schadt, Rodenbach (DE);
Christine Knuehl, Darmstadt (DE);
Manja Friese-Hamim, Moerfelden-Walldorf (DE); Bayard R. Huck, Sudbury, MA (US); Andreas Goutopoulos, Boston, MA (US); Nadia Brugger, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 25 days.

(21) Appl. No.: 14/234,356

(22) PCT Filed: Jun. 15, 2012

(86) PCT No.: PCT/US2012/042567
§ 371 (c)(1),
(2), (4) Date: Feb. 28, 2014

(87) PCT Pub. No.: WO2013/022519
PCT Pub. Date: Feb. 14, 2013

(65) Prior Publication Data
US 2014/0228379 A1 Aug. 14, 2014

Related U.S. Application Data

(60) Provisional application No. 61/521,841, filed on Aug. 10, 2011.

(51) Int. Cl.
| C07D 487/04 | (2006.01) |
| A61K 31/519 | (2006.01) |
| A61K 45/06 | (2006.01) |
| C07D 471/04 | (2006.01) |
| A61P 35/00 | (2006.01) |
| A61P 37/00 | (2006.01) |
| A61P 9/10 | (2006.01) |
| A61P 25/28 | (2006.01) |
| A61P 27/06 | (2006.01) |

(52) U.S. Cl.
CPC ............... *A61K 31/519* (2013.01); *A61K 45/06* (2013.01); *C07D 471/04* (2013.01)

(58) Field of Classification Search
CPC .................................................. C07D 487/04
See application file for complete search history.

(56) References Cited

U.S. PATENT DOCUMENTS 6,069,134 A  5/2000  Roth et al.

FOREIGN PATENT DOCUMENTS

| WO | 00/50032 A1 | 8/2000 |
| WO | 2006/116713 A1 | 11/2006 |
| WO | 2011/017142 A1 | 2/2011 |

OTHER PUBLICATIONS

Weinstein-Oppenheimer et al., Pharmacol. Ther.; 88, 229-279 (2000).
Stéphane Raeppel, et al., Bioorganic & Medicinal Chemistry Letters; 20, 2745-2749 (2010).
J.M. O'Toole et al., Cancer Res.; 66, 9162-9170 (2006).
P.C. Ma, et al., Cancer Metastasis Rev.; 22, 309-325 (2003).
C.W. Birchmeier, et al., Nat. Rev. Mol. Cell Biol.; 4(12), 915-925 (2003).
J.G. Christensen et al., Cancer Letters; 225, 1-26 (2005).
S. Corso et al., Trends Mol. Med.; 11, 284-292 (2005).
C. Boccaccio and P.M. Comoglio, Nat. Rev. Cancer; 6, 637-645 (2006).
B. Peruzzi and D.P. Bottaro, Clinical Cancer Res.; 12(12), 3657-3660 (2006).
B.S. Knudsen and G. Vande Woude, Cur. Opin. Genet. Dev.; 18, 87-96 (2008).
L. Toschi and P.A. Jänne, Clin. Cancer Res.; 14(19), 5941-5946 (2008).
I. Dussault and S.F. Bellon, Anti-Cancer Agents Med. Chem.; 9, 221-229 (2009).
N. A. Cipriani et al., Lung Cancer; 63, 169-179 (2009).
J. Porter, Expert Opin. Ther. Patents; 20, 159-177 (2010).
T.L. Underiner et al., Anti-Cancer Agents Med. Chem.; 10, 7-27 (2010).
Y.Zhang et al., Cancer Res; 68 (16), 6680-6687 (2008).
L.Liu et al., J. Med. Chem.; 51, 3688-3691 (2008).
G.M. Schroeder et al., J. Med. Chem.; 52, 1251-1254 (2009).
M. Yoshida et al., Int. J. Pharm.; 115, 61-67 (1995).
Tyle P., Pharmaceutical Research; 3(6), 318-326 (1986).
Khwaja et al., EMBO; 16(10), 2783-2793 (1997).
White et al., Oncogene; 20(48), 7064-7072 (2001).
Davies, Stephen P. et al., Biochemical J.; 351, 95-105 (2000).
Alessi et al., FEBS Letters; 399(3), 333-338 (1996).
Campos-González, R. and Glenney, Jr., J.R., J. Biol. Chem.; 267(21), 14535-14538 (1992).
Sorg et al., J. of Biomolecular Screening; 7, 11-19 (2002).
Sills et al., J. of Biomolecular Screening; 7, 191-214 (2002).

*Primary Examiner* — Susanna Moore
(74) *Attorney, Agent, or Firm* — Merck Patent GmbH

(57) ABSTRACT

Compounds of the formula I

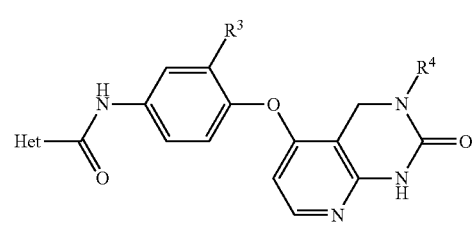

in which Het, $R^3$ and $R^4$ have the meanings indicated in Claim 1,
are inhibitors of RON and can be employed, for the treatment of cancer.

13 Claims, No Drawings

PYRIDO-PYRIMIDINE DERIVATIVES

BACKGROUND OF THE INVENTION

The invention had the object of finding novel compounds having valuable properties, in particular those which can be used for the preparation of medicaments.

The present invention relates to pyrido-pyrimidine compounds that are capable of inhibiting one or more kinases. The compounds find applications in the treatment of a variety of disorders, including cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The present invention relates to compounds and to the use of compounds in which the inhibition, regulation and/or modulation of signal transduction by kinases, in particular receptor tyrosine kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

In particular, the present invention relates to compounds and to the use of compounds in which the inhibition, regulation and/or modulation of signal transduction by RON (récepteur d'origine nantais) plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

S. Raeppel et al. describe potent RON receptor tyrosine kinase inhibitors with residual activity against the closely related c-Met or potent dual inhibitory activity against RON and c-Met, such as N-(3-fluoro-4-(2-substituted-thieno[3,2-b]pyridine-7-oxy)phenyl)-1-phenyl-5-(trifluoromethyl)-1H-pyrazole-4-carboxamides, in Bioorganic & Medicinal Chemistry Letters 20 (2010) 2745-2749 as potential anti-cancer therapeutics.

ImClone Systems (now a division of Eli Lilly & Co.) developed IMC-41A10, a human IgG1 monoclonal antibody that binds with high affinity to human RON RTK (receptor tyrosine kinase) and blocks MSP (macrophage stimulating protein) ligand binding (J. M. O'Toole et al., Cancer Res. 2006, 66, 9162). IMC-41A10 inhibited tumor growth by 50-60% in several human xenograft tumor models including colon, lung and pancreatic carcinoma models.

Small molecule inhibitors of RON have been described as well. These chemical entities inhibit both RON and the closely related c-Met kinase. c-Met is found to be activated in a large number of different cancers and small molecule inhibitors targeting Met/RON are presently under clinical evaluation in patients with solid tumors:

(a) For recent reviews see: P. C. Ma, G. Maulik, J. Christensen and R. Salgia, *Cancer Metastasis Rev.* 22 (2003), p. 309.

(b) C. W. Birchmeier, W. Birchmeier, E. Gherardi and G. F. Vande Woude, *Nat. Rev. Mol. Cell Biol.* 4 (2003), p. 915.

(c) J. G. Christensen, J. Burrows and R. Salgia, *Cancer Lett.* 225 (2005), p. 1.

(d) S. Corso, P. M. Comoglio and S. Giordano, *Trends Mol. Med.* 11 (2005), p. 284.

(e) C. Boccaccio and P. M. Comoglio, *Nat. Rev. Cancer* 6 (2006), p. 637.

(f) B. Peruzzi and D. P. Bottaro, *Clin. Cancer Res.* 12 (2006), p. 3657.

(g) B. S. Knudsen and G. Vande Woude, *Cur. Opin. Gen. Dev.* 18 (2008), p. 87.

(h) L. Toschi and P. A. Jänne, *Clin. Cancer Res.* 14 (2008), p. 5941.

(i) I. Dussault and S. F. Bellon, *Anti-Cancer Agents Med. Chem.* 9 (2009), p. 221.

(j) N. A. Cipriani, O. O. Abidoye, E. Vokes and R. Salgia, *Lung Cancer* 63 (2009), p. 169.

(k) J. Porter, *Expert Opin. Ther. Patents* 20 (2010), p. 159.

(l) T. L. Underiner, T. Herbertz and S. J. Miknyoczki, *Anti-Cancer Agents Med. Chem.* 10 (2010), p. 7.

For example, a potent small-molecule dual inhibitor of c-Met/RON was disclosed by Amgen:

J. Zhang et al., Cancer Res. 2008, 68, 6680;

L. Liu et al., J. Med. Chem. 2008, 51, 3688.

This quinoline based compound having the 1-(2-hydroxy-2-methylpropyl)-5-methyl-3-oxo-2-phenyl-2,3-dihydro-1H-pyrazole-4-carboxamide head group

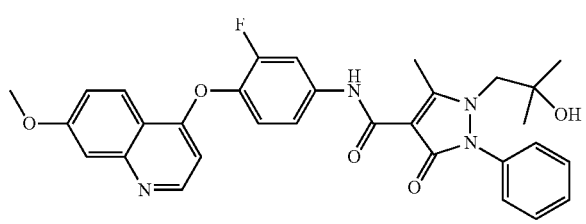 [SMILES: COc1ccc2c(Oc3ccc(NC(=O)c4c(C)n(CC(C)(C)O)n(-c5ccccc5)c4=O)cc3F)ccnc2c1]

inhibits both Met and RON enzymes and demonstrates antitumor activity in a colorectal xenograft model in mice.

Bristol-Myers Squib describes BMS-777607

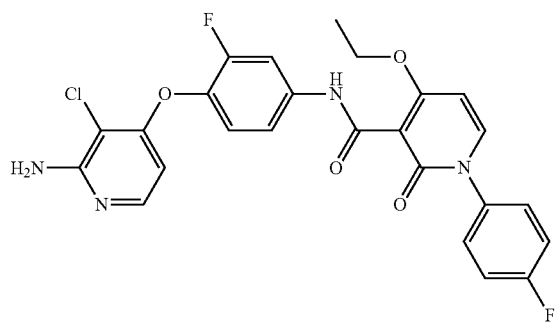 [SMILES: CCOc1ccn(-c2ccc(F)cc2)c(=O)c1C(=O)Nc1ccc(Oc2ccnc(N)c2Cl)c(F)c1]

as a new pyridine based selective and orally efficacious inhibitor of the Met/RON kinase superfamily that has advanced into phase I clinical trials (G. M. Schroeder et al., J. Med. Chem. 2009, 52, 1251).

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore suitable for the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined. The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

In addition, the compounds according to the invention can be used to achieve additive or synergistic effects in certain existing cancer chemotherapies and radiotherapies and/or to restore the efficacy of certain existing cancer chemotherapies and radiotherapies.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a target kinase together in such a manner that the compound can affect the enzyme activity of the kinase either directly; i.e., by interacting with the kinase itself or indirectly; i.e., by interacting with another molecule on which the catalytic activity of the kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

For any compound used in this invention, a therapeutically effective amount, also referred to herein as a therapeutically effective dose, can be estimated initially from cell culture assays. For example, a dose can be formulated in animal models to achieve a circulating concentration range that includes the IC50 or the IC100 as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the LD50 and the ED50. The dose ratio between toxic and therapeutic effect is the therapeutic index and can be expressed as the ratio between LD50 and ED50. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition, (see, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day.

Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

Preferred diseases or disorders that the compounds described herein may be useful in preventing, treating and/or studying are cell proliferative disorders, especially cancer such as, but not limited to, papilloma, blastoglioma, Kaposi's sarcoma, melanoma, lung cancer, ovarian cancer, prostate cancer, squamous cell carcinoma, astrocytoma, head cancer, neck cancer, skin cancer, liver cancer, bladder cancer, breast cancer, lung cancer, uterus cancer, prostate cancer, testis carcinoma, colorectal cancer, thyroid cancer, pancreatic cancer, gastric cancer, hepatocellular carcinoma, leukemia, lymphoma, Hodgkin's disease and Burkitt's disease.

PRIOR ART

Other heterocyclic derivatives and their use as anti-tumour agents have been described in WO 2006/116713 A1.

S. Raeppel et al. describe potent RON receptor tyrosine kinase inhibitors in Bioorganic & Medicinal Chemistry Letters 20 (2010) 2745-2749 as potential anti-cancer therapeutics.

SUMMARY OF THE INVENTION

The invention relates to compounds of the formula I

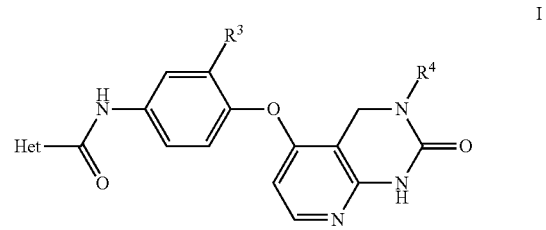

in which
Het denotes imidazolyl, pyrazolyl, oxazolyl, isoxazolyl, thiazolyl or triazolyl, each of which is substituted by $R^1$ and $R^2$,
$R^1$ denotes $Ar^1$,
$R^2$ denotes A',
$R^3$ denotes F or Cl,
$R^4$ denotes H, $CH_2Ar^2$ or A,
$Ar^1$ denotes phenyl, which is unsubstituted or mono-, di- or trisubstituted by Hal, A, OH, OA, $CONH_2$, COOH, COOA, CN, CHO, COA, $SO_2A$, NHCOA and/or, $SO_2NH_2$,
$Ar^2$ denotes phenyl, which is unsubstituted or mono-, di- or trisubstituted by Hal, A, OH, OA, $CONH_2$, COOH, COOA, CN, CHO, COA, $SO_2A$, NHCOA and/or, $SO_2NH_2$,
A' denotes unbranched or branched alkyl having 1-6 C atoms, in which 1-7H atoms may be replaced by F,
A denotes unbranched or branched alkyl having 1-10 C atoms, in which one or two non-adjacent CH and/or $CH_2$ groups may be replaced by N, O, S atoms and/or by —CH=CH— groups and/or in addition 1-7H atoms may be replaced by F,
and pharmaceutically usable salts, tautomers and stereoisomers thereof, including mixtures thereof in all ratios.

The invention also relates to the optically active forms (stereoisomers), salts, the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides.

Of course, the invention also relates to the solvates of the salts.

The term pharmaceutically usable derivatives is taken to mean, for example, the salts of the compounds according to the invention and also so-called prodrug compounds. The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1-12 and pharmaceutically usable salts, tautomers and stereoisomers thereof, characterised in that
a) a compound of the formula II Het-CO-L    II in which Het has the meanings indicated in Claim 1 and
L denotes Cl, Br, I or a free or reactively functionally modified OH group,
is reacted with a compound of the formula III

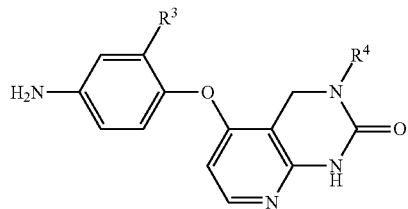

III in which $R^3$ and $R^4$ have the meaning indicated in Claim 1, and/or a base or acid of the formula I is converted into one of its salts.

Above and below, the radicals Het, $R^1$, $R^2$, $R^3$ and $R^4$ have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two CH and/or $CH_2$ groups in A may also be replaced by N, O or S atoms and/or by —CH=CH— groups. A thus also denotes, for example, 2-methoxyethyl.

More preferably, A denotes unbranched or branched alkyl having 1-6 C atoms, in which one or two non-adjacent CH and/or $CH_2$ groups may be replaced by N and/or O atoms and/or in addition 1-7H atoms may be replaced by F.

A' denotes alkyl, is unbranched (linear) or branched, and has 1, 2, 3, 4, 5 or 6 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A' preferably denotes alkyl having 1, 2, 3 or 4 C atoms, preferably methyl, ethyl, propyl, isopropyl, butyl, isobutyl, sec-butyl, tert-butyl or trifluoromethyl.

$Ar^1$ denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

$Ar^1$ particularly preferably denotes phenyl.

$Ar^2$ denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

$Ar^2$ preferably denotes phenyl, which is unsubstituted or mono- or disubstituted by OH and/or OA, $Ar^2$ particularly preferably denotes phenyl or o-, m- or p-methoxyphenyl.

Het preferably denotes 1-$R^1$-5-$R^2$-1H-pyrazol-4-yl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ie, which conform to the formula I and in which the radicals not designated in greater detail have the meaning indicated for the formula I, but in which in Ia Het denotes 1-$R^1$-5-$R^2$-1H-pyrazol-4-yl;
in Ib $Ar^1$ denotes phenyl;
in Ic $Ar^2$ denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl;
in Id A denotes unbranched or branched alkyl having 1-6 C atoms, in which one or two non-adjacent CH and/or $CH_2$ groups may be replaced by N and/or O atoms and/or in addition 1-7H atoms may be replaced by F;
in Ie Het denotes 1-$R^1$-5-$R^2$-1H-pyrazol-4-yl
$R^1$ denotes $Ar^1$,
$R^2$ denotes A',
$R^3$ denotes F or Cl,
$R^4$ denotes H, $CH_2Ar^2$ or A,
$Ar^1$ denotes phenyl,
$Ar^2$ denotes phenyl, which is unsubstituted or mono- or disubstituted by OH and/or OA,
A' denotes unbranched or branched alkyl having 1-6 C atoms, in which 1-7H atoms may be replaced by F,
A denotes unbranched or branched alkyl having 1-6 C atoms, in which one or two non-adjacent CH and/or $CH_2$ groups may be replaced by N and/or O atoms and/or in addition 1-7H atoms may be replaced by F,
and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions.

Use can also be made here of variants known per se which are not mentioned here in greater detail.

Compounds of the formula I can preferably be obtained by reacting compounds of the formula II with a compound of formula III.

The compounds of the formula II and of formula III are generally known. If they are novel, however, they can be prepared by methods known per se.

In the compounds of the formula II, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

The cleavage of an ether is carried out by methods as are known to the person skilled in the art.

A standard method of ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar.

Esters can be saponified, for example, using acetic acid or using NaOH or KOH in water, water/THF or water/dioxane, at temperatures between 0 and 100°.

Alkylations on the nitrogen are carried out under standard conditions, as are known to the person skilled in the art.

The compounds of the formulae I can furthermore be obtained by liberating them from their functional derivatives by solvolysis, in particular hydrolysis, or by hydrogenolysis.

It is furthermore possible to convert a compound of the formula I into another compound of the formula I.

Preferably, a group $R^4 \neq H$ is removed, preferably by treatment with an anorganic or organic acid like TFA, to give a compound of formula I, wherein $R^4$=H.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)-methylamine(tromethamine), but this is not intended to represent a restriction.

Compounds of the present invention which contain basic nitrogen-containing groups can be quaternised using agents such as $(C_1$-$C_4)$alkyl halides, for example methyl, ethyl, isopropyl and tert-butyl chloride, bromide and iodide; di$(C_1$-$C_4)$ alkyl sulfates, for example dimethyl, diethyl and diamyl sulfate; $(C_{10}$-$C_{18})$alkyl halides, for example decyl, dodecyl, lauryl, myristyl and stearyl chloride, bromide and iodide; and aryl$(C_1$-$C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient.

Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and the pharmaceutically usable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the pharmaceutically usable salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or the pharmaceutically usable salts, tautomers and stereoisomers thereof, including mixtures thereof in all ratios, and at least one further medicament active ingredient.

The invention also relates to a set (kit) consisting of separate packs of (a) an effective amount of a compound of the formula I and/or the pharmaceutically usable salts, tautomers and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or the pharmaceutically usable salts, tautomers and stereoisomers thereof, including mixtures thereof in all ratios, and an effective amount of a further medicament active ingredient in dissolved or lyophilised form.

USE

The invention relates to the compounds of formula I for the use for the treatment of cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The invention relates to the use of compounds of formula I for the preparation of a medicament for the treatment of cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The invention relates to a method of treating a mammal having a disease selected from cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease, wherein the method comprises administering to a mammal a therapeutically effective amount of a compound of formula I.

The present compounds are suitable as pharmaceutical active ingredients for mammals, especially for humans, in the treatment and control of cancer diseases and inflammatory diseases.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

The present invention encompasses the use of the compounds of the formula I and/or physiologically acceptable salts, tautomers and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts, tautomers and solvates thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the cancer disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radio-therapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamine-platinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(di-methylamino)ethyl]-N-methylamino]ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

TEST FOR THE INHIBITION OF RON

Inhibition of MSP (Macrophage Stimulating Protein) Induced pRON in Cellular Assays To determine potency and efficacy of RON kinase inhibitors in inhibiting ligand induced RON phosphorylation, compounds were tested in cell based assays as described below. Inhibition of ligand induced pRON (phosphoRON) in MDA-MB453 cells (cell based electrochemiluminescence assay (ECLA)): MDA-MB453 cells (DSMZ ACC65) were serum starved, pretreated with 100 μM Sodium Orthovanadate (1 h, 37° C., 5% $CO_2$) and pre-incubated with compounds (serial dilutions, starting concentration 30 μM) in serum-free media for 45 min at 37° C., 5% $CO_2$. Cells were stimulated with 250 ng/ml MSP (R&D Systems, #4306-MS) for 20 min, supernatants discarded and cells lysed in cold NP-40 lysis buffer (1% NP-40, 20 mM Tris, pH8.0, 137 mM NaCl, 10% glycerole, 2 mM EDTA, protease inhibitor cocktail set III (Calbiochem), phosphatase inhibitor cocktail set II (Calbiochem)). MA6000 96 well plates (MSD, # L15XB) were blocked with 3% block A (MSD) in PBS, pH7.4, 0.05% Tween20 and coated with RON specific capture antibody (R&D Systems, # MAB691). Cell lysates were added and incubated for 2 h at room temperature (RT). Biotinylated anti-phospho Tyrosine antibody (R&D Systems, # BAM1676) and sulfo tag streptavidin reagent (MSD, #R32AD) were used for detection.

In-Vitro (Enzyme) Assay for Determination of the Efficacy of Inhibitors of RON Kinase-Mediated Effects The kinase assay was carried out as 384-well FlashPlate assay. As test plates 384-well streptavidine coated FlashPlate microtitre plates from Perkin Elmer (USA) were used. The components of the kinase reaction were pipetted into the assay plate. 4.5 nM of GST tagged human recombinant RON kinase (Life technologies), 500 nM of biotinylated peptide substrate RDILDREYYSVQQHRH-amide (autophosphorylation site derived peptide substrate, custom-made) and 2 μM of ATP (with 0.5 μCi of <33>P-ATP/well) were incubated in a total volume of 50 μl (50 mM of HEPES, 5 mM of MgCl2, 2 mM of DTT, 0.1% of BSA, 0.01% Igepal®CA630, 1% DMSO, pH 7.5) in the presence or absence of test substance (10 concentrations) at 22 [deg.] C. for 30 min. The reaction was stopped using 50 μl of 200 mM EDTA solution. After incubation for a further 80 min at room temperature, the supernatants were removed by suction, and the wells were washed three times with 100 μl of 0.9% NaCl solution each time. The radioactivity was measured using a Topcount scintillation counter (PerkinElmer, USA). The IC50 values were calculated using Assay explorer (Table X).

EXAMPLE 1

The preparation of 1-phenyl-5-trifluoromethyl-1H-pyrazole-4-carboxylic acid [3-fluoro-4-(2-oxo-1,2,3,4-tetrahydro-pyrido[2,3-d]pyrimidin-5-yloxy)-phenyl]-amide ("A1") is carried out analogously to the following scheme ene. The mixture is stirred at room temperature (RT) for 30 min. The solvent is then removed by distillation in vacuo. The residue is dissolved in 20 ml of tetrahydrofuran (THF), and 0.62 g (16.4 mmol, 1.5 eq.) of . . . is added. The mixture is stirred at RT for 4 hours. 2 ml of methanol are then added, and the mixture is stirred at RT for 5 min. The solvent is removed by distillation in vacuo, and the residue is taken up in 100 ml of saturated sodium bicarbonate solution. The mixture is extracted twice with 150 ml of ethyl acetate (EA). The combined organic phases are dried using magnesium sulfate (MgSO₄), filtered and evaporated in vacuo, giving 3.1 g (75%) of 2, which is employed in the next step without further purification.

1.2 3.10 g (8.20 mmol) of 2 are dissolved in 40 ml of dichloromethane (DCM), and 10 ml of trifluoroacetic acid are added. The mixture is stirred at RT for 2 hours. The reaction mixture is then evaporated to dryness in vacuo. The residue is taken up in 150 ml of EA and extracted with 100 ml of saturated sodium bicarbonate solution. The organic phase is

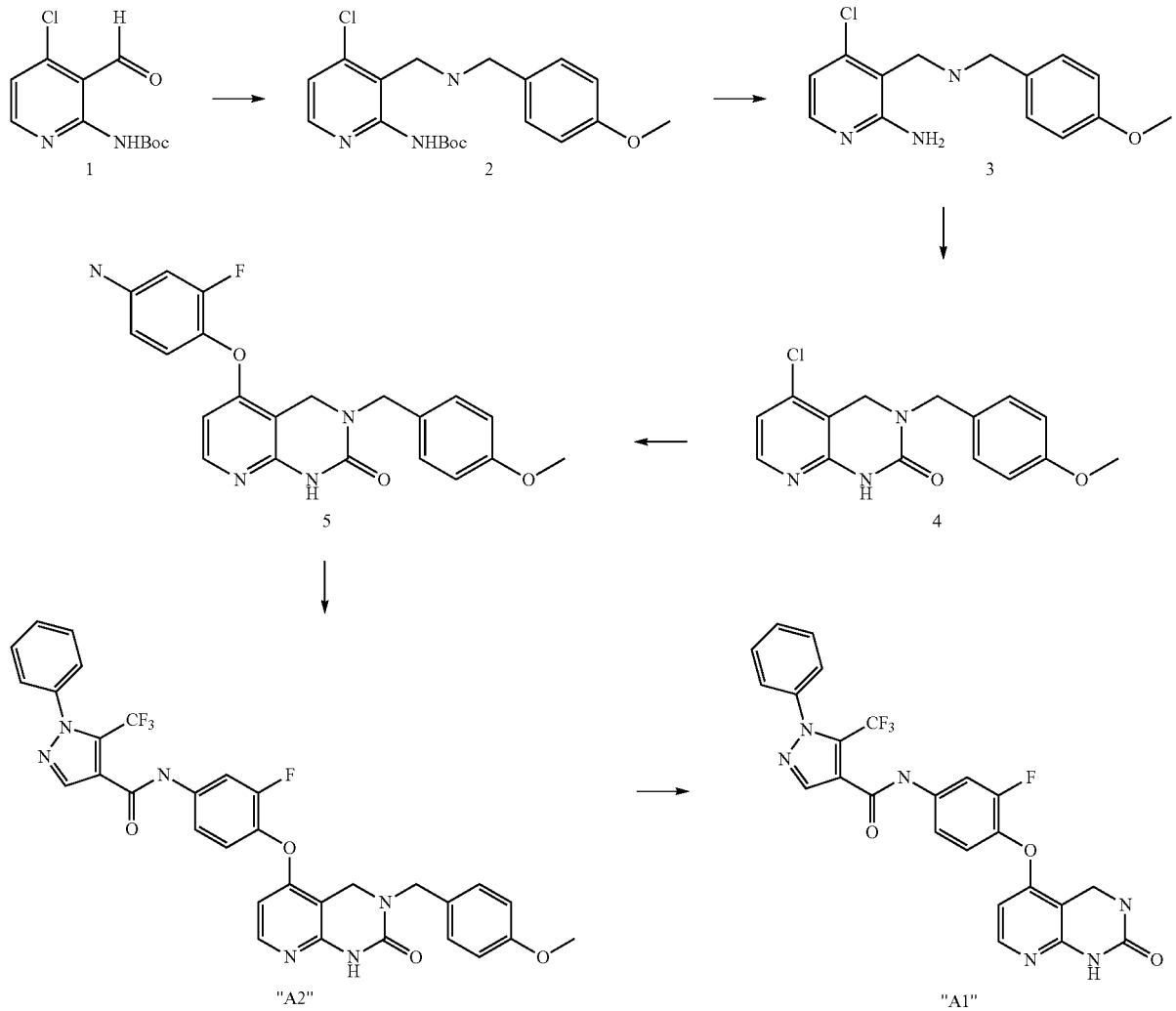

1.1 1.41 ml (10.9 mmol) of 4-methoxybenzylamine are added to a solution of 2.80 g (10.9 mmol) of tert-butyl (4-chloro-3-formylpyridin-2-yl)carbamate in 20 ml of toludried using MgSO₄, filtered and evaporated in vacuo. The crude product 3 (2.21 g, 97%) is employed in the next step without further purification.

1.3 2.21 g (7.96 mmol) of 3 are dissolved in 30 ml of acetonitrile, and 1.36 g (8.39 mmol, 1.05 eq.) of 1,1'-carbonyldiimadazole are added. The mixture is stirred at RT for 24 hours. The solvent is then removed by distillation in vacuo. The residue is taken up in water, filtered off and washed with a little methanol, giving 2.05 g (85%) of 4, which is employed in the next step without further purification.

1.4 400 mg (1.31 mmol) of 4, 250 mg (1.97 mmol, 1.5 eq.) of 4-amino-2-fluoro-phenol and 854 mg (2.62 mmol, 2.0 eq.) of caesium carbonate are suspended in 10 ml of DMF and stirred at 150° C. for 4 hours. The solvent is then removed by distillation in vacuo, and the residue is chromatographed on about 50 g of silica gel with the eluent DCM/methanol (99/1 v/v), giving 222 mg (43%) of 5 as a crystalline solid.

1.5 216 mg (0.84 mmol) of 1-phenyl-5-trifluoromethylpyrazole-4-carboxylic acid are dissolved in 5 ml of DCM, 0.09 ml (1.26 mmol, 1.5 eq.) of thionyl chloride is added, and the mixture is refluxed for 1 hour. The reaction mixture is then evaporated in vacuo. The residue is dissolved in 5 ml of pyridine, and 222 mg (0.67 eq.) of 5 are added. The mixture is stirred at RT for 1 hour. The reaction mixture is then stirred into 30 ml of water and filtered. The residue is dissolved in 50 ml of DCM, dried using MgSO$_4$ and chromatographed on 30 g of silica gel with the eluent DCM/methanol (98/2 v/v), giving 304 mg (86%) of 1-phenyl-5-trifluoromethyl-1H-pyrazole-4-carboxylic acid {3-fluoro-4-[3-(4-methoxy-benzyl)-2-oxo-1,2,3,4-tetrahydro-pyrido[2,3-d]pyrimidin-5-yloxy]-phenyl}-amide ("A2") as colourless crystals;

$^1$H NMR (500 MHz, DMSO-d$_6$) δ [ppm] 3.74 (s, 3H), 4.41, (s, 2H), 4.54 (s, 2H), 6.17 (d, 1H, J=5.8 Hz), 7.36 (t, 1H, J=9.0 Hz), 7.58-7.49 (m, 3H), 7.67-7.58 (m, 3H) 8.33 (s, 1H), 9.87 (s, 1H), 10.82 (s, 1H).

1.6 304 mg (0.48 mmol) of 6 are dissolved in 5 ml of TFA and stirred at 80° C. for 16 hours. After the mixture has been cooled to RT, 20 ml of diethyl ether are added, and the precipitate is filtered off with suction and washed with ether. It is taken up in about 15 ml of acetone, heated to the boil, filtered off with suction again and washed with acetone, giving 225 mg (91%) of "A1";

$^1$H NMR (500 MHz, DMSO-d$_6$) δ [ppm] 10.83 (s, 1H), 9.53 (d, J=1.5 Hz, 1H), 8.34 (s, 1H), 7.94 (t, J=4.8 Hz, 1H), 7.90 (dd, J=12.8, 2.3 Hz, 1H), 7.68-7.60 (m, 3H), 7.60-7.51 (m, 3H), 7.40 (t, J=9.0 Hz, 1H), 7.03 (d, J=1.4 Hz, 1H), 6.20 (d, J=5.8 Hz, 1H), 4.45 (d, J=0.7 Hz, 2H).

Following compounds are prepared analogously:

| compound nr. | structure/name |
|---|---|
| "A3" | 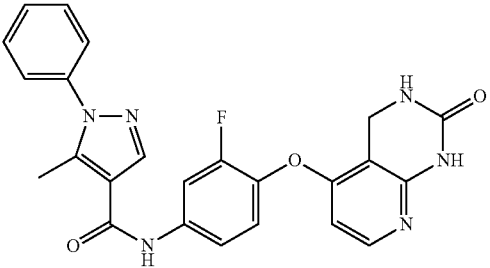 [SMILES: Cc1c(C(=O)Nc2ccc(Oc3ccnc4c3CNC(=O)N4)c(F)c2)cnn1-c1ccccc1]<br>5-methyl-1-phenyl-1H-pyrazole-4-carboxylic acid [3-fluoro-4-(2-oxo-1,2,3,4-tetrahydro-pyrido[2,3-d]pyrimidin-5-yloxy)-phenyl]-amide<br>$^1$H NMR (500 MHz, DMSO-d$_6$) δ [ppm] 10.24 (s, 1H), 9.80 (s, 1H), 8.39 (s, 1H), 8.05-7.94 (m, 2H), 7.67-7.46 (m, 6H), 7.37 (t, J = 9.1 Hz, 1H), 7.25-7.15 (m, 1H), 6.36-6.24 (m, 1H), 4.47 (d, J = 6.3 Hz, 2H), 2.56 (s, 3H) |
| "A4" | 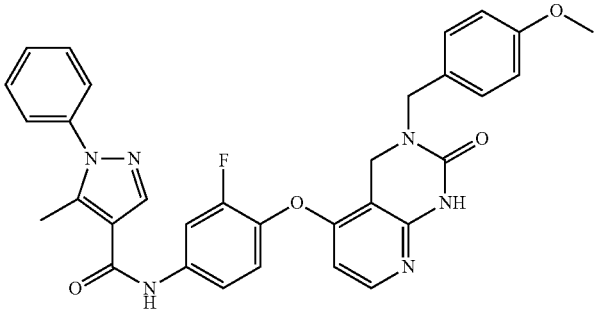 [SMILES: COc1ccc(CN2Cc3c(Oc4ccc(NC(=O)c5cnn(-c6ccccc6)c5C)cc4F)ccnc3NC2=O)cc1]<br>5-methyl-1-phenyl-1H-pyrazole-4-carboxylic acid {3-fluoro-4-[3-(4-methoxy-benzyl)-2-oxo-1,2,3,4-tetrahydro-pyrido[2,3-d]pyrimidin-5-yloxy]-phenyl}-amide<br>$^1$H NMR (500 MHz, DMSO-d$_6$) δ [ppm] 10.12 (s, 1H), 9.86 (s, 1H), 8.31 (s, 1H), 7.99-7.87 (m, 2H), 7.64-7.45 (m, 6H), 7.36-7.25 (m, 3H), 6.93 (d, J = 8.6, 2H), 6.16 (d, J = 5.6, 1H), 4.54 (s, 2H), 4.41 (s, 2H), 3.74 (s, 3H), 2.55 (s, 3H). |

IC$_{50}$ values of compounds according to the invention inhibiting RON

| Compound No. | RON enzyme assay IC$_{50}$ [nM] | RON cell assay IC$_{50}$ [nM] |
|---|---|---|
| "A1" | 4.3 | 79 |
| "A2" | | |
| "A3" | 10 | 130 |
| "A4" | | |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of the formula I

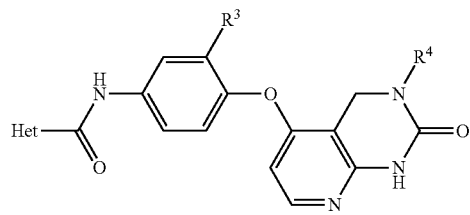

in which:
Het denotes imidazolyl, pyrazolyl, oxazolyl, isoxazolyl, thiazolyl or triazolyl, each of which is substituted by R$^1$ and R$^2$,
R$^1$ denotes Ar$^1$,
R$^2$ denotes A',
R$^3$ denotes F or Cl,
R$^4$ denotes H, CH$_2$Ar$^2$ or A,
Ar$^1$ denotes phenyl, which is unsubstituted or mono-, di- or trisubstituted by A, OH, OA, CONH$_2$, COOH, COOA, CN, CHO, COA, SO$_2$A, NHCOA and/or, SO$_2$NH$_2$,
Ar$^2$ denotes phenyl, which is unsubstituted or mono-, di- or trisubstituted by A, OH, OA, CONH$_2$, COOH, COOA, CN, CHO, COA, SO$_2$A, NHCOA and/or, SO$_2$NH$_2$,
A' denotes unbranched or branched alkyl having 1-6 C atoms, in which 1-7 H atoms may be replaced by F,
A denotes unbranched or branched alkyl having 1-10 C atoms, in which one or two non-adjacent CH and/or CH$_2$ groups may be replaced by N, O, S atoms and/or by —CH=CH— groups and/or in addition 1-7 H atoms may be replaced by F,
and pharmaceutically usable salts, tautomers and stereoisomers thereof.

2. A compound according to claim 1, in which:
Het denotes 1-R$^1$-5-R$^2$-1H-pyrazol-4-yl
and pharmaceutically usable salts, tautomers and stereoisomers thereof.

3. A compound according to claim 1, in which:
Ar¹ denotes phenyl,
and pharmaceutically usable salts, tautomers and stereoisomers thereof.

4. A compound according to claim 2, in which:
Ar¹ denotes phenyl,
and pharmaceutically usable salts, tautomers and stereoisomers thereof.

5. A compound according to claim 1 in which:
Ar² denotes phenyl, which is unsubstituted or mono- or disubstituted by OH and/or OA, and pharmaceutically usable salts, tautomers and stereoisomers thereof.

6. A compound according to claim 2 in which:
Ar² denotes phenyl, which is unsubstituted or mono- or disubstituted by OH and/or OA, and pharmaceutically usable salts, tautomers and stereoisomers thereof.

7. A compound according to claim 3, in which:
Ar² denotes phenyl, which is unsubstituted or mono- or disubstituted by OH and/or OA, and pharmaceutically usable salts, tautomers and stereoisomers thereof.

8. A compound according to claim 4, in which:
Ar² denotes phenyl, which is unsubstituted or mono- or disubstituted by OH and/or OA, and pharmaceutically usable salts, tautomers and stereoisomers thereof.

9. A compound according to claim 1, in which:
A denotes unbranched or branched alkyl having 1-6 C atoms, in which one or two non-adjacent CH and/or $CH_2$ groups may be replaced by N and/or O atoms and/or in addition 1-7 H atoms may be replaced by F and pharmaceutically usable salts, tautomers and stereoisomers thereof.

10. A compound according to claim 1, in which:
Het denotes 1-$R^1$-5-$R^2$-1H-pyrazol-4-yl
$R^1$ denotes Ar¹,
$R^2$ denotes A',
$R^3$ denotes F or Cl,
$R^4$ denotes H, $CH_2Ar^2$ or A,
Ar¹ denotes phenyl,
Ar² denotes phenyl, which is unsubstituted or mono- or disubstituted by OH and/or OA,
A' denotes unbranched or branched alkyl having 1-6 C atoms, in which 1-7 H atoms may be replaced by F,
A denotes unbranched or branched alkyl having 1-6 C atoms, in which one or two non-adjacent CH and/or $CH_2$ groups may be replaced by N and/or O atoms and/or in addition 1-7 H atoms may be replaced by F,
and pharmaceutically usable salts, tautomers and stereoisomers thereof.

11. A compound according to claim 1, selected from the group consisting of:

| compound nr. | name |
|---|---|
| "A1" | 1-phenyl-5-trifluoromethyl-1H-pyrazole-4-carboxylic acid [3-fluoro-4-(2-oxo-1,2,3,4-tetrahydro-pyrido[2,3-d]pyrimidin-5-yloxy)-phenyl]-amide |
| "A2" | 1-phenyl-5-trifluoromethyl-1H-pyrazole-4-carboxylic acid {3-fluoro-4-[3-(4-methoxy-benzyl)-2-oxo-1,2,3,4-tetrahydro-pyrido[2,3-d]pyrimidin-5-yloxy]-phenyl}-amide |
| "A3" | 5-methyl-1-phenyl-1H-pyrazole-4-carboxylic acid [3-fluoro-4-(2-oxo-1,2,3,4-tetrahydro-pyrido[2,3-d]pyrimidin-5-yloxy)-phenyl]-amide |
| "A4" | 5-methyl-1-phenyl-1H-pyrazole-4-carboxylic acid {3-fluoro-4-[3-(4-methoxy-benzyl)-2-oxo-1,2,3,4-tetrahydro-pyrido[2,3-d]pyrimidin-5-yloxy]-phenyl}-amide | and pharmaceutically usable salts, tautomers and stereoisomers thereof.

12. Process for the preparation of compounds of the formula I according to claim 1 and pharmaceutically usable salts, tautomers and stereoisomers thereof, characterized in that:
a) a compound of the formula II Het-CO-L      II in which Het has the meanings indicated in claim 1 and
L denotes Cl, Br, I or a free or reactively functionally modified OH group,
is reacted with a compound of the formula III

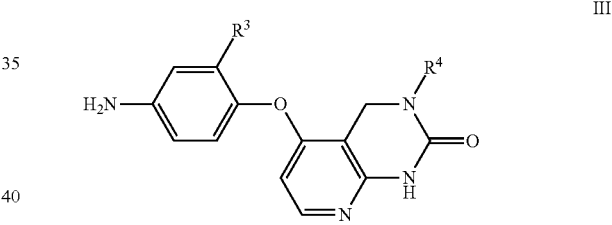

in which $R^3$ and $R^4$ have the meaning indicated in claim 1, and/or
a base or acid of the formula I is converted into one of its salts.

13. A medicament comprising at least one compound of the formula I according to claim 1 or pharmaceutically usable salts, tautomers and stereoisomers thereof and optionally excipients or adjuvants.

* * * * *